(12) United States Patent
Batarseh (10) Patent No.: US 8,673,366 B2
(45) Date of Patent: Mar. 18, 2014

(54) CHEMOTHERAPEUTIC AND PROPHYLACTIC PHARMACEUTICAL COMPOSITIONS

(76) Inventor: Kareem I. Batarseh, Fairfax Station, VA (US)

( * ) Notice: Subject to any disclaimer, the term of this patent is extended or adjusted under 35 U.S.C. 154(b) by 1664 days.

(21) Appl. No.: 10/867,214

(22) Filed: Jun. 14, 2004

(65) Prior Publication Data

US 2005/0276795 A1    Dec. 15, 2005

(51) Int. Cl.
*A01N 59/16* (2006.01)
*A01N 55/02* (2006.01)
*A01N 33/08* (2006.01)

(52) U.S. Cl.
USPC ........... 424/617; 514/492; 514/727; 424/616; 424/94.4

(58) Field of Classification Search
USPC .................. 424/617, 616, 94.4; 514/492, 727
See application file for complete search history.

(56) References Cited

U.S. PATENT DOCUMENTS

| 5,356,803 | A | * | 10/1994 | Carpenter et al. | ............. | 435/200 |
| 5,357,636 | A | * | 10/1994 | Dresdner et al. | ................ | 2/161.7 |
| 6,046,160 | A | * | 4/2000 | Obi-Tabot | .......................... | 514/2 |
| 6,187,743 | B1 | * | 2/2001 | Obi-Tabot | .......................... | 514/2 |
| 6,238,678 | B1 | * | 5/2001 | Oblong et al. | ................. | 424/401 |

OTHER PUBLICATIONS

Razak Lajis "The abuse and toxicity of zinc" www.prn2.usm.my/mainsite/bulletin/sun/1996/sun5.html, published May 17, 2003.*
Braun "Regulation of iron uptake minimizes iron-mediated oxidative stress" Journal of Biosciences vol. 23, No. 4,Oct. 1998 pp. 483-489.*
Engineer et al. "Effects of Cisplatin-Induced Nephrotox1city on Gentam1cin Pharmacokinetics in Rats" Drug Metabolism and Disposition vol. 15, No. 3, 1987 pp. 329-334.*
Legler et al. "Synthesis and Antimicrobial Activity of Silver Complexes With Arginine and Glutamic Acid" Pharmaceutical Chemistry Journal vol. 35, No. 9, 2001 pp. 501-503.*
David A. Rowley and Barry Halliwell "Superoxide-Dependent Formation of Hydroxyl Radicals From NADH and NADPH in the Presence of Iron Salts" FEBS Letters vol. 142, No. 1, 1982, pp. 39-41.*
Haiduc et al., "Rhodium, Iridium, Copper and Gold Antitumor Organometallic Compounds (Review)," In Vivo, Jul.-Aug. 1989, 3(4); pp. 285-293 (abstract only).

(Continued)

*Primary Examiner* — Rosanne Kosson (57) ABSTRACT

The present invention provides pharmaceutical compositions and methods for making the same, which are highly effective against cancer, viruses, amoebae, bacteria (both gram-negative and -positive), fungi, algae, bacterial spores, yeast, and the like. The compounds preferably rely on employing the synergistic effect of organo-metal compounds and the concomitant generation of reactive oxygen species (ROS) through the agency of reducing cofactors. The aqueous solution may be condensed and dried using conventional methods available to those skilled in the art to produce gels as well as solids, such as tablets or powders. Solid forms include tablets, capsules, suppositories, and the like or mixtures thereof. In addition, the solid form of the present compositions may be activated upon solubilization in a liquid.

23 Claims, 2 Drawing Sheets

% Inhibition obtained on the Present Invention "Drug" and CIS PLA for Both Cell Lines.

(56) References Cited

OTHER PUBLICATIONS

Seongman Kang and Robert D. Wells "Zinc Destabilizes DNA Watson-Crick Pairs at AGCT" The Journol Biological Chemistry vol. 269, No. 13, Issue of Apr. 1, pp. 9528-9532, 1994.*

J. E. Sprietsma "Modern diets and diseases: NO—zinc balance" Medical Hypotheses (1999) 53(1), 6-16.*

Koppenol, "The Basic Chemistry of Nitrogen Monoxide and Peroxynitrite," Free Radical Biology and Medicine, Sep. 1998, vol. 25, Issues 4-5, pp. 385-391 (abstract only).

Gatto et al., "Coralyne and Related Compounds as Mammalian Topoisomerase I and Topoisomerase II Poisons," Bioorg. Med. Chem., Jun. 1996, 4(6), pp. 781-791 (abstract only).

Hurst et al., "Leukocytic Oxygen Activation and Microbicidal Oxidative Toxins," Critical Reviews in Biochemistry and Molecular Biology, vol. 24, Issue 4, pp. 271-328 (abstract only), 1989.

Caruso et al., "Anticancer Titanium Agents," Expert Opinion on Therapeutic Patents, 2001, vol. 11, No. 6, pp. 969-979 (abstract only).

Yamashita et al., "Induction of Mammalian DNA Topoisomerase I and II Mediated DNA Cleavage by Saintopin, A New Antitumor Agent from Fungus," Biochemistry, 1991, 30, pp. 5838-5845.

Haber et al., "The Catalytic Decomposition of Hydrogen Peroxide by Iron Salts," Proceedings of the Royal Society of London, Series A, Mathematical and Physical Sciences, Nov. 15, 1934, vol. 147, No. 861, pp. 332-351.

Stermitz et al., "Synthesis and Biological Activity of Some Antitumor Benzophenanthridinium Salts," The Journal of Medicinal Chemistry, 1975, vol. 18, No. 7, pp. 708-713.

Rothenborg-Jensen et al., "Linker Length in Podophyllotoxin-Acridine Conjugates Determines Potency In Vivo and In Vitro as Well as Specificity Against MDR Cell Lines," Anti-Cancer Drug Design, 2001, 16, pp. 305-315.

Bailly, "Topoisomerase I Poisons and Suppressors as Anticancer Drugs," Current Medicinal Chemistry, 2000, 7, pp. 39-58.

Lindahl, "Worthy of a Detour," Nature, vol. 298, Jul. 29, 1982, pp. 424-425.

Forbes et al., "Sparse Initial Entrapment of Systemically Injected *Salmonella typhimurium* Leads to Heterogenous Accumulation within Tumors," Cancer Research, vol. 63, Sep. 1, 2003, pp. 5188-5193.

Znati et al., "Irradiation Reduces Interstitial Fluid Transport and Increases the Collagen Content in Tumors," Clinical Cancer Research, vol. 9, Nov. 15, 2003, pp. 5508-5513.

Jain et al., "What Brings Pericytes to Tumor Vessels?" The Journal of Clinical Investigation, vol. 112, No. 8, Oct. 2003, pp. 1134-1136.

Fujii et al., "Induction of Mammalian DNA Topoisomerase I-mediated DNA Cleavage and DNA Winding by Bulgarein," The Journal of Biological Chemistry, vol. 268, No. 18, Jun. 25, 1993, pp. 13160-13165.

Luo et al., "Three Chemically Distinct Types of Oxidants Formed by Iron-Mediated Fenton Reactions in the Presence of DNA," Proc. Natl. Acad. Sci. USA, vol. 9, Dec. 1994, pp. 12438-12442.

Robinson et al., "Starvation Enhances Hepatic Free Radical Release Following Endotoxemia," Journal of Surgical Reasearch, vol. 69, 1997, pp. 325-330.

Imlay et al., "Toxic DNA Damage by Hydrogen Peroxide Through the Fenton Reaction in Vivo and In Vitro," Science, vol. 240, Apr. 1998, pp. 640-642.

Spencer et al., "DNA Strand Breakage and Base Modification Induced by Hydrogen Peroxide Treatment of Human Respiratory Tract Epithelial Cells," Federation of European Biochemical Societies, vol. 374, 1995, pp. 233-236.

Sun et al., "Synthesis and Evaluation of Terbenzimidazoles as Topoisomerase I Inhibitors," Journal of Medicinal Chemistry, vol. 38, No. 18, 1995, pp. 3638-3644.

Kim et al., "Substituted 2,5'-Bi-1H-Benzimidazoles: Topoisomerase I Inhibition and Cytotoxicity," Journal of Medicinal Chemistry, vol. 39, 1996, pp. 992-998.

Imlay et al., "Bimodal Pattern of Killing of DNA-Repair-Defective or Anoxically Grown *Escherichia coli* by Hydrogen Peroxide," Journal of Bacteriology, vol. 166, No. 2, May 1986, pp. 519-527.

O'Reilly et al., "Angiostatin: A Novel Angiogenesis Inhibitor that Mediates the Suppression of Metastases by a Lewis Lung Carcinoma," Cell, vol. 79, Oct. 21, 1994, pp. 315-328.

Jain, "Molecular Regulation of Vessel Maturation," Nature Medicine, vol. 9, No. 6, Jun. 2003, pp. 685-693.

Jain, "Vascular and Interstitial Barriers to Delivery of Therapeutic Agents in Tumors," Cancer and Metastasis Reviews, vol. 9, 1990, pp. 253-266.

Britigan et al., "Binding of Myeloperoxidase to Bacteria: Effect of Hydroxyl Radical Formation and Susceptibility to Oxidant-Mediated Killing," Biochimica et Biophysica Acta, vol. 1290, 1996, pp. 231-240.

O'Reilly et al., "Endostatin: An Endogenous Inhibitor of Angiogenesis and Tumor Growth," Cell, vol. 88, Jan. 24, 1997, pp. 277-286.

Chen et al., "A New Mammalian DNA Topoisomerase I Poison Hoechst 33342: Cytotoxicity and Drug Resistance in Human Cell Cultures," Cancer Research, vol. 53, Mar. 15, 1993, pp. 1332-1337.

Yamashita et al., "Induction of Mammalian DNA Topoisomerase I Mediated DNA Cleavage by Antitumor Indolocarbazole Derivatives," Biochemistry, vol. 31, 1992, pp. 12069-12075.

Fridovich, "The Biology of Oxygen Radicals," Science, vol. 201, Sep. 8, 1978, pp. 875-880.

Beauchamp et al., "A Mechanism for the Production of Ethylene from Methional," The Journal of Biological Chemistry, vol. 245, No. 18, Sep. 25, 1970, pp. 4641-4646.

Gutman et al., "On the Complexation of Ferric Ions by Reduced Nicotinamide Adenine Dinucleotide," Biochemistry, vol. 12, No. 12, 1973, pp. 2314-2317.

Land et al., "One-Electron Reactions in Biochemical Systems as Studied by Pulse Radiolysis," Biochimica et Biophysica Acta, vol. 234, 1971, pp. 34-42.

Caruso et al., "Synthesis, Structure, and Antitumor Activity of a Novel Tetranuclear Titanium Complex," J. Med. Chem., vol. 43, 2000, pp. 3665-3670.

\* cited by examiner

Figure 1. Hydroxyl Radical Production.

Figure 2. % Inhibition obtained on the Present Invention "Drug" and CIS PLA for Both Cell Lines.

Figure 3. % Inhibition Obtained on the Present Invention "Drug" and Cyclophosphamide for the Four Cell Lines.

CHEMOTHERAPEUTIC AND PROPHYLACTIC PHARMACEUTICAL COMPOSITIONS

FIELD OF THE INVENTION

In general, the invention relates to controlling cancer and pathogens and more particularly relates to cytotoxic, chemotherapeutic agents and microbicides which are preferably nontoxic, noncorrosive, and nonirritant to mammals and plants which are highly effective against viruses, amoebae, bacteria (both gram-negative and -positive), fungi, algae, bacterial spores, yeast, and the like. The present invention can be employed as a chemotherapeutic agent, a general disinfectant and antipathogenic, treatment of microbiological infections, sterilization of medical articles, surfaces and areas, surgical equipment and devices and the like. My invention can also be used in vivo and in vitro to disinfect transplant tissues and organs, vascular and skin grafts, blood, including red blood cells, blood platelets, and blood plasma, hence rendering organs, or other tissues and blood constituents to be safer for therapeutic, diagnostic or experimental use. The present invention can also be employed in disinfecting formulations for inhibiting the growth of targeted microorganisms in vitro, particularly in applications where biomedical devices, including but not limited to surgical instruments, catheters, dental appliances, bandages, shunts, heart valves, wound dressing and wound drain tubes, needles, examination and surgical gloves, sutures, intraocular devices, contact lenses and the like where the biomedical device is subsequently used in vivo where the device or devices are contacted with host tissue. The compositions of the present invention can also be used for veterinary medicine in the treatment of animals, including exotic and farm animals.

BACKGROUND OF THE INVENTION

With the advent of new technological, scientific advances and findings in the fields of oncology, microbiology and epidemiology, there has been a growing interest among scientists and physicians to develop new medicines having carcinostatic effects and methods to control the spread of diseases and inhibit and greatly reduce the infectivity of certain harmful microorganisms. Pathogens such as viruses, bacteria, and fungi have been known to cause a plethora of human, animal and plant diseases and illnesses along with the concomitant contamination of food, and biological and environmental samples. Of particular interest are those pathogens, which are associated with incurable and often fatal diseases such as acquired immune deficiency syndrome or commonly referred to as AIDS, the various forms of hepatitis, cytomegalovirus, and the like. Bacterial infections such as those linked to the *Bacillus* genus, which form stable spores that can withstand and sustain harsh conditions, and extreme temperatures are other such microorganisms; for example, *B. antharcis* leads to a fatal disease in humans, domestic, agricultural and wild animals. Human contamination results from contact with infected animals, and recently another route of contamination is via terrorist activities and/or biological warfare. Other examples of bacteria that can have deleterious effects, which develop resistance, include the genus *Staphylococcus* that often can cause fatal infections, *Pneumococci* that can cause meningitis and pneumonia, and *Enterococci* that can cause infections of surgical wound, urinary tract and blood.

The current treatments for cell proliferation diseases such as cancer and psoriasis employ cytotoxic heavy metals, which inhibit cell division and DNA replication. Examples of such metals are gold, titanium, tin, copper, vanadium, iridium, rhodium, and the like (Haiduc, I. & Silvestru, C., *In Vivo*, 4, 285 (1989); Caruso, F., et al., *J. Med. Chem*, 43, 3665 (2000); and Caruso, F., et al., *Expert. Opin. Ther. Patents,* 11, 969 (2001)). The most prominent and promising family of cytotoxic agents is those referred to as "oxaliplatin", also known as L-OHP. These agents utilize platinum as the heavy metal and are considered a third generation platinum complexes. These include those disclosed following the procedure described in Kidani et al., U.S. Pat. No. 4,169,846; Tanaka, U.S. Pat. Nos. 5,290,961, 5,298,642, 5,338,874, 5,420,319, 5,959,133 and European patent application No. 715,854; SmithKline Beecham, U.S. Pat. No. 5,633,016; Debiopharm, International patent applications WO 94/12193 and WO 01/15691, European patent application No. 1121117 and U.S. Pat. No. 5,716,988; Pharmacia & Upjohn Co., U.S. Pat. No. 6,287,593; Sanofi-Synthelabo, U.S. Pat. Nos. 6,063,780 and 6,306,902; BioNumerik, U.S. Pat. No. 6,066,666; and Bristol-Myers Squibb, International patent application WO 01/66102, incorporated herein in their entirety by reference. This class of drugs has entered the market through its in vitro and in vivo cytotoxic activity, and its good clinical tolerance, e.g., the absence of renal or auditory toxicity being combined with a low hematotoxicity.

Other methods have relied upon the use of ultra-violet irradiated silver fluoride solutions containing silver as a source of germicide activities, such as U.S. Pat. No. 3,422,183, incorporated herein in its entirety by reference. However, such techniques require expensive equipment and large amounts of electricity.

Hydrogen peroxide is a strong oxidizing agent, and it has been used for the past 40 years as a disinfectant. Its main advantage is that it does not produce toxic residue or by-products. It has been used ubiquitously as an indirect food additive, as a disinfectant in hospitals, as a decontamination and purification agent of industrial wastewater, and as a cleaning agent for exhaust air. Nonetheless, it decomposes readily to form water and oxygen, and has high sensitivity to sunlight and UV rays. Therefore, it is not suited for long-term use since recontamination cannot be circumvented.

In 1880, the Swiss botanist Carl van Nageli observed that highly diluted silver solutions have an algicidal effect. To describe this effect he coined the term "Oligodynamic". Colloidal silver, which is a pure, all-natural substance consisting of sub-microscopic clusters of silver ions held in suspension in de-ionized water by tiny positive charges on the silver ions, is a powerful prophylactic antibiotic which was used for years with no known side effects. It acts as an inhibitor disabling particular enzymes which bacteria, fungi, and viruses used in their mode of metabolism.

Based on this oligodynamic property, U.S. Pat. No. 4,915,955, incorporated in its entirety herein by reference, combines the germicidal effects of hydrogen peroxide with silver, an inorganic acid, and an organic stabilizer at concentrations of 10-35 mg/l to combat many forms of bacteria and viruses. The process is based on silver ions, with the aid of hydrogen peroxide, damaging the protective biofilms of these microorganisms. Hence, this method depends solely on killing germs intercellularly.

U.S. Pat. No. 6,242,009, incorporated herein in its entirety by reference, describes the formation of metal complexes suitable as disinfectants and sanitizers to combat pathogenic microorganisms. It relies on using metal ions and amino acids to form complexes, which serve as carriers for metals, in order to diffuse into the intra-cellular medium of such microorganisms where it exhibits its biocidal activities. The composition can be prepared by mixing a metal salt compound in an aqueous solution, and an inorganic acid at room temperature to adjust the pH of the solution; adding at least on an equimolar basis, depending on the valency of the metals, at least one amino acid to form an insoluble metal complex while homogenizing the mixture; and depending on its use, the resultant solution can then be proportioned with various ratios to make suitable disinfectants by adding appropriate amount of distilled-deionized water and/or hydrogen peroxide.

U.S. Pat. No. 6,630,172, incorporated herein in its entirety by reference, delves on the use of organo-metallic complexes that can be employed as microbicides to combat pathogenic microorganisms. It is based on using metal ions and potassium sodium tartrate to form organo-metallic chelates where these chelates can exhibit its microbicidal activities. The composition can be prepared by mixing a metal salt compound in an aqueous solution, and an inorganic acid at room temperature to adjust the pH of the solution; adding potassium sodium tartrate in at least one fourth of the molar amount with respect to the valency of the designated metal while homogenizing the mixture; depending on its use, the resultant solution can then be proportioned with various ratios to make suitable disinfectants by adding appropriate amount of distilled-deionized water and/or hydrogen peroxide. Optionally, amino acids can be added to the mixture to enhance metal chelation.

Although various robust methods and techniques have been employed to combat cancer and pathogens, cancer and antimicrobial therapy suffers from various deficiencies. Cancer therapy nowadays involves a multi-modality approach of one or a combination of radiation, chemotherapy, hormone therapy, immunotherapy, and antiangiogenic drugs (non-cytotoxic class of anti-tumor agents that inhibit the development of new blood vessels from older ones). Surgery, on the other hand, involves the bulk removal of diseased tissue. While surgery is sometimes effective in removing neoplasms, or tumors (unregulated and disorganized proliferation of cell) located at certain sites, for example, in the breast, colon, and skin, it cannot be used in the treatment of tumors located in other areas, such as the backbone, nor in the treatment of disseminated neoplastic conditions such as leukemia. If portions of the primary tumor cannot be removed or if it is believed to have metastasized, systemic drug therapy is given to kill residual cancerous cells through targeting of actively dividing cells.

There are difficulties associated with cancerous compounds in that effective treatment is hampered due to lack of specificity and difficulty in delivering these agents to the site of the carcinogenic tumors. This is especially true with using chemotherapeutic and cytotoxic agents with neoplasms where within the intra-or-inner-region of neoplasm the network of blood capillaries is too small for such agents to be delivered (Jain, R., Cancer Metastasis Rev., 9, 253 (1990); Forbes, N. S., et al., Cancer Research, 63, 5188 (2003); Znati, C. A., et al., Clinical Cancer Research, 9, 5508 (2003); Jain, R. K., Nature Medicine, 9, 685 (2003); Jain, R. K., & M. F. Booth, J. Clinical Investigation, 112, 1134 (2003); and Jain, R. K. Vascular and Interstitial Biology of Tumors (Chapter 9). In M. Abeleff, J. Armtage, M. Kastan, G. McKenna, J. Niederhuber, and D. Meloni (ed.), Clinical Oncology, 3rd Edition, in press. Elsevier, Philadelphia, Pa.). These regions are commonly exist in most major classes of solid tumors such as those associated with breast, head and neck, pancreatic, stomach, ovarian, cervical, lung, and prostate tumors. The present organic moieties, therefore, have smaller molecular weights from which smaller size chemotherapeutic molecules can be developed to combat neoplasms.

Additionally, there is the problem of the patient developing a resistance with the continual and the prolong use of such agents. Also, the many adverse side effects associated with the current systemic therapeutic methods used for the treatment of cancer make the current invention an excellent candidate for alternative therapy. These induced side effects significantly impact the quality of life of the patient and sometimes dramatically influence the patient compliance with the treatment regiment. These complications include cytopenia, cachexia, infections, mucositis, especially in patients receiving high doses of chemotherapy with bone marrow rescue or radiation therapy, alopecia, pruritis, urticaria, and angioedema, and many others related to pulmonary, cardiac, reproductive and endocrine. These complications are the major dose-limiting toxicity and can lead to hospitalization of the patient and analgesics for the alleviation of pain. In addition, the toxicity of these agents renders them to be particularly dangerous and risk of contamination during manufacturing and reconstitution to workers, pharmacists, medical personnel, and nurses.

The overwhelming use of antibiotic and antiviral drugs has resulted in a worldwide epidemic, especially when strains of various pathogens appear resistant to antibiotics and antiviral medications. This problem is becoming a major crisis since these new strains of bacteria cause deadly infections, which are extremely difficult to treat, resulting in necrosis and death in many instances. Aside from microorganisms' mutation, they are also associated with numerous negative side effects, including killing the flora, fatigue, gastrointestinal upsets, candidiasis, severe skin rashes, kidney and renal infections, diarrhoea, colitis, hearing loss and many more.

With respect to biocides that rely on the use of chemical adjuvants such as aldehydes, phenols, alcohol, potassium permanganate, and chlorine and certain chlorine containing compounds have many disadvantages associated with them. This is mainly due to toxicity that leads to tissue necrosis upon administration and pulmonary injuries after inhalation of volatile gases and fumes. In addition, the corrosive nature of such compounds renders them unsuitable for disinfection of sensitive equipment, and people coming into contact with these substances can develop skin irritation and suffer from long time illnesses, which in some cases can be fatal; not to mention the unpleasant taste and odor associated with these chemicals. In addition, formation of mutagenic and carcinogenic agents, and genetically resistant strains are also some of their disadvantages. Notwithstanding, such compounds have afforded a way to battle these harmful microorganisms and their effectiveness has been unequivocally demonstrated.

Accordingly, there is an immediate need to develop and design new generation of chemotherapeutic, and antipathogenic agents that are able to overcome the above-described disadvantages, and lower the infectivity and mortality of those associated with pathogens. Thus, formulation of novel chemotherapeutic and antimicrobial compositions is necessarily ad hoc. Such compositions should overcome one or more of the above-described disadvantages, and concurrently being nontoxic, noncorrosive and nonirritant to the recipient. Also, it is an object of the present invention to provide compounds, which upon administration rapidly break down to release their chemotherapeutic agent, and realize their cytotoxic effect with minimum negative side effects.

SUMMARY OF THE INVENTION

In accordance with the present invention, new compositions and methods are provided for combating cancer, neoplasms, and for the decontaminating or inhibiting the growth of viruses, amoebae, bacteria (both gram-negative and -positive), fungi, algae, bacterial spores, yeast, and the like whether in vitro or in vivo. In one broad aspect, the present invention combines the synergistic effect of chelated organic metal complexes hereinafter referred to as R-M where R is an organic moiety and M is a metal that is chemotherapeutic and/or biocidal to pathogens and the concomitant generation of reactive oxygen species (ROS) or free radicals through the agency of reducing cofactors to form such compositions, and contacting such compositions with pathogenic microorganisms.

Within the present context, free radicals imply an atom or group of atoms with an unpaired electron that are generally capable of existing in an independent reactive state. The underlying mechanism responsible for the killing activities of these compositions and methods is therefore the use of these two factors in a synergistic or a concerted fashion. Such compositions comprise an aqueous milieu, e.g., distilled-deionized water, an organic complex of the formula R-M such as those found in U.S. Pat. Nos. 6,242,009 and 6,630,172, reducing cofactors, e.g., nicotinamide adenine dinucleotide (NADH), nicotinamide adenine dinucleotide phosphate (NADPH), flavin adenine dinucleotide (FADH), flavin adenine dinucleotide phosphate (FADPH), and mixtures thereof, an oxidizing metal catalyst present in an effective amount so as to promote NAD(P)H (refers to both NADH and NADPH) oxidation, e.g., ferric iron, and an oxidative disinfectant, e.g., hydrogen peroxide. The preparation is done at room temperature (e.g., 20-30° C.) and under acidic conditions.

Examples of the metal ion M include, but are not limited to, cations of silver including colloidal silver, copper, zinc, mercury, manganese, chromium, nickel, cadmium, arsenic, cobalt, aluminum, lead, iron, rhodium, iridium, selenium, platinum, gold, titanium, tin, barium, bismuth, vanadium, iron, strontium, antimony, and salts thereof, and the like, and any combination thereof.

Generally, a coenzyme can contact and reduce a metal catalyst. The reduced metal catalyst may then function to facilitate the production of ROS from the ROS generating species, ordinarily through the donation of an electron. Any number of reducing cofactors/coenzymes may be used. More specifically, the coenzymes (reduced form shown), nicotinamide adenine dinucleotide (NADH), nicotinamide adenine dinucleotide phosphate (NADPH) and/or flavin adenine dinucleotide (FADH) and flavin adenine dinucleotide phosphate (FADPH) are particularly effective as electron carriers. Similarly, any number of oxidixing metal catalysts/cofactors capable of generating ROS can be utilized. More specifically, Cu, Fe, K, Mg, Mn, Mo, Ni, Se, and/or Zn are particularly effective catalysts. These catalysts may be used in their pure form or may be combined with a salt and then be introduced into a solvent.

The amount of each constituents of the present invention depends on a plethora of factors, including the compositions' function, the time needed to accomplish this function, severity of contamination, etc. If the formulation is to be used to kill a large number of microorganisms and if the environment contains high concentrations of microorganisms, larger and higher concentrations are then necessary. Therefore, it is prudent to know a priori information about the extent of contamination in an effort to properly formulate the invention with respect to the concentrations of the present composition's chemical constituents.

Representative compositions of the present invention comprise the following: the amount of R-M is such that found in U.S. Pat. Nos. 6,242,009 and 6,630,172; the amount of cofactor, preferably NADH or NADPH, added ranges from one to three times the amount of the molar concentration of the catalyzing metal being used, preferably ferric iron, with a preferred molar ratio of 2:1 $\{[NADH]/[Fe^{+3}]\}$, where the amount of ferric iron ranges between 0.05 to 100 µM and the amount of peroxide, preferably hydrogen peroxide, added ranges preferably from 1 to 100 mM, corresponding to 34 to 3400 ppm.

A particularly useful application of the compositions of the present invention is as a chemotherapeutic agent, treatment of neoplasms, a general disinfectant and antipathogenic, treatment of microbiological infections, sterilization of medical articles, surfaces and areas, surgical equipment and devices and the like. The invention is also amenable to be used in vivo and in vitro to disinfect transplant tissues and organs, vascular and skin grafts, blood, including red blood cells, blood platelets, and blood plasma, hence rendering organs, or other tissues and blood constituents to be safer for therapeutic, diagnostic or experimental use. The present invention can also be employed in disinfecting formulations for inhibiting the growth of targeted microorganisms in vitro, particularly in applications where biomedical devices, including but not limited to surgical instruments, catheters, dental appliances, bandages, shunts, heart valves, wound dressing and wound drain tubes, needles, examination and surgical gloves, sutures, intraocular devices, contact lenses and the like where the biomedical device is subsequently used in vivo where the device or devices are contacted with host tissue.

Certain embodiments of the present compositions are non-toxic to humans and animals, and therefore can be safely ingested or administered via nasal, buccal, vaginal, rectal, and topical, and can be contacted via subcutaneous, intradermal, intramascular injections. Other routes of delivery of the present compositions to the site of infection include impregnation into absorptive materials, e.g., bandages, gauze, or coating on solid phase materials such as zippers, staples, and the like. It will be appreciated that the actual preferred method and order of administration will vary according to the particular disease and host being treated. The optimal method and order of administration of the subject composition for a given set of conditions can be ascertained by those skilled in the art using conventional techniques and in view of the information set out herein.

The compositions further comprise pharmaceutically acceptable stabilizers, adjuvants, diluents, bioactive chemicals such as antivirals, antibiotics, antitumors, vitamins, minerals, and the like and mixtures thereof. Additionally, biological buffers that are nontoxic to cells can comprise the present invention.

It is to be understood that the preceding general discussion and the discussion which follows are considered explanatory and exemplary in nature, and are solely intended to give additional merits of the current invention, as claimed. It is also to be understood that the preferred embodiments of my invention are not limited to the use of the above-mentioned constituents, but it also encompasses the use of a broad spectrum of substances that are within the skill of chemical artisans and repertoire to utilize. Emphasis should also be directed on the fact that steps taken to prepare the present compositions can be done in different orders; for instance, the compositions can be premixed with certain substances and diluted with, for example, water prior to commercial distribution or can be sold as a concentrate while dilution and/or addition of other chemicals can be performed at the site of use. Hence, the specific embodiments and the illustrative examples, which follow, are in no way limit the claims of this invention.

DETAILED DESCRIPTION OF THE INVENTION

The present invention relates generally to the combination of two components. The first component is an organic (R) metal (M) complex (R-M), such as described in U.S. Pat. Nos. 6,242,009 and 6,630,172, incorporated in their entirety by reference herein. This R-M complex can be combined with a system for generating one or more reactive oxygen species (ROS) with the combination preferably producing a synergistic effect that can be highly effective in the destruction of microbes and/or cancerous or pre-cancerous cells.

The present invention is broadly directed to compositions to control cancer and pathogens and more particularly relates to chemotherapeutic and antimicrobial agents, that are preferably nontoxic, noncorrosive, and nonirritant to mammals and plants which are highly effective against cancer, viruses, amoebea, bacteria (both gram-negative and -positive), fungi, algae, bacterial spores, yeast, and the like. The present invention has a myriad of applications and uses and can be employed as an anticancerous agent, a general disinfectant and antipathogenic, treatment of microbiological infections, sterilization of medical articles, surfaces and areas, surgical equipment and devices and the like. It can also be used in vivo and in vitro to disinfect transplant tissues and organs, vascular and skin grafts, blood, including red blood cells, blood platelets, and blood plasma, hence rendering organs, or other tissues and blood constituents to be safer for therapeutic, diagnostic or experimental use. The present invention can also be employed in disinfecting formulations for inhibiting the growth of targeted microorganisms in vitro, particularly in applications where biomedical devices, including but not limited to surgical instruments, catheters, dental appliances, bandages, shunts, heart valves, wound dressing and wound drain tubes, needles, examination and surgical gloves, sutures, intraocular devices, contact lenses and the like where the biomedical device is subsequently used in vivo where the device or devices are contacted with host tissue.

The present invention can also be used for the treatment or prevention of neoplasia disorders including, actinic keratoses, adenocarcinoma, adenoid cycstic carcinoma, adenomas, adenosarcoma, astrocytic tumors, basal cell carcinoma, bronchial gland carcinomas, carcinosarcoma, choriod plexus papilloma/carcinoma, clear cell carcinoma, endometrial hyperplasia, Ewing's sarcoma, Wilm's tumor, gastrinoma, germ cell tumors, hepatic adenoma, hepatic adenomatosis, hepatocellular carcinoma, insulinoma, large cell carcinoma, malignant melanoma, oligodendroglial, osteosarcoma, pituitary tumors, pulmonary blastoma, renal cell carcinoma, sarcoma, serous carcinoma, soft tissue carcinomas, somatostatin-secreting tumor, and vipoma.

Aerobic organisms, which derive their energy from the reduction of oxygen, routinely generate amounts of $.O^-_2$, $H_2O_2$, and $.OH$ that inevitably form during the metabolism of oxygen, especially in the reduction of oxygen by the electron transfer system of mitochondria. These three species, referred to as reactive oxygen species (ROS), are used to kill pathogenic microorganisms, and a major contributor to neutrophil-mediated cytotoxicity (Hurst, J. K. & Barerette, W. C., *CRC Crit. Rev. Biochem. Mol. Biol.*, 24, 271(1989)).

Some chemicals have a reactive nature such that pathogens cannot develop a resistance to them. Reactive oxygen species (ROS) or free radicals, in particular the hydroxyl radical, are one such group of chemicals. ROS or free radicals, in particular the hydroxyl radical, is an etiological agent for a deluge of conditions and can react with all biological macromolecules (lipids, proteins, nucleic acids, and carbohydrates) and can cause significant damage and cytotoxicity (Fridovich, I., *Sci.*, 201, 875 (1978)). The mechanism of formation at physiological pH includes the activation of a membrane-bound enzyme (NAD(P)H)-dependent oxidase system. This complex reduces oxygen to superoxide anion ($.O^-_2$), which rapidly dismutes through the agency of metalloenzymes superoxide dismutases (SOD) to form hydrogen peroxide ($H_2O_2$) where it can then be converted catalytically to hydroxyl radicals (.OH). Superoxides and hydrogen peroxide per se are not highly reactive and cytotoxic, and relatively mild oxidants that belie the severity of their direct involvement in damaging organic substrates; hence, their inherent cytotoxicity is attributed to their intracellular generation of injurious OH, which requires the presence of $Fe^{+2}$. The hydroxyl radical is an extremely powerful oxidant that reacts at nearly diffusion-controlled rates with organic biomolecules.

The present invention encompasses any method of producing ROS when coupled with the R-M species. The rate of formation of ROS can be allowed to proceed unassisted or may be enhanced through the use of rate increasing agents, like compounds such as enzymes/co-enzymes or catalysts/co-factors.

Generally, a coenzyme can contact and reduce a metal catalyst. The reduced metal catalyst may then function to facilitate the production of ROS from the ROS generating species, ordinarily through the donation of an electron. Any number of reducing cofactors/coenzymes may be used. More specifically, the coenzymes (reduced form shown), nicotinamide adenine dinucleotide (NADH), nicotinamide adenine dinucleotide phosphate (NADPH) and/or flavin adenine dinucleotide (FADH) are particularly effective as electron carriers. Similarly, any number of oxidixing metal catalysts/cofactors capable of generating ROS can be utilized. More specifically, Cu, Fe, K, Mg, Mn, Mo, Ni, Se, and/or Zn are particularly effective catalysts. These catalysts may be used in their pure form or may be combined with a salt and then be introduced into a solvent.

The overall mechanism can be represented by the following reaction scheme:

$$O_2 + e^- \xrightarrow{NAD+} O^-_2 \qquad (1)$$

The reduction of molecular oxygen with oxidized nicotinamide adenine dinucleotide ($NAD^+$), Reaction 1, occurs very rapidly to form the free radical superoxide oxygen species. The coenzyme (a prosthetic group) $NAD^+$ is the most common hydrogen acceptor and oxidizing agent in biological processes: $NAD^+ + 2e^- + 2H^+ \rightarrow NADH + H^+$. The molecule contains two major parts, namely, a) an adenosine diphosphate portion, linked through a ribose to b) nicotinamide ring. It is the nicotinamide ring that is able to be reduced readily and serves as an oxidizing agent.

Superoxide can act as an oxidant (by accepting electrons) or as a reductant (by donating electrons). It potentiates .OH production by two paths, namely, by reducing $Fe^{+3}$ and recycling the available free iron to $Fe^{+2}$, and releasing free iron from iron stores such as ferritin. Under biological conditions, the main reaction of superoxide is to react with itself to produce hydrogen peroxide and oxygen, a reaction known as "dismutation". Superoxide dismutation can be spontaneous or can be catalyzed by a metalloenzyme superoxide dismutase (SOD); thus, (2)

A metal such as Cu, Mn, and Fe mediates the catalytic activities of SOD. Subsequently, the hydrogen peroxide formed can then react with ferrous iron to produce hydroxyl radicals with the aid of SOD according to:

(3)

In this process, superoxide acts as a reducing agent since it donates one electron to reduce the ferric iron that acts as the catalyst to convert hydrogen peroxide ($H_2O_2$) into the hydroxyl radical (.OH). The reduced metal (ferrous iron or $Fe^{+2}$) then catalyzes the breaking of the oxygen-oxygen bond of hydrogen peroxide to produce a hydroxyl radical (.OH) and a hydroxide ion ($^-$OH); thus, (4)

Figure 1:
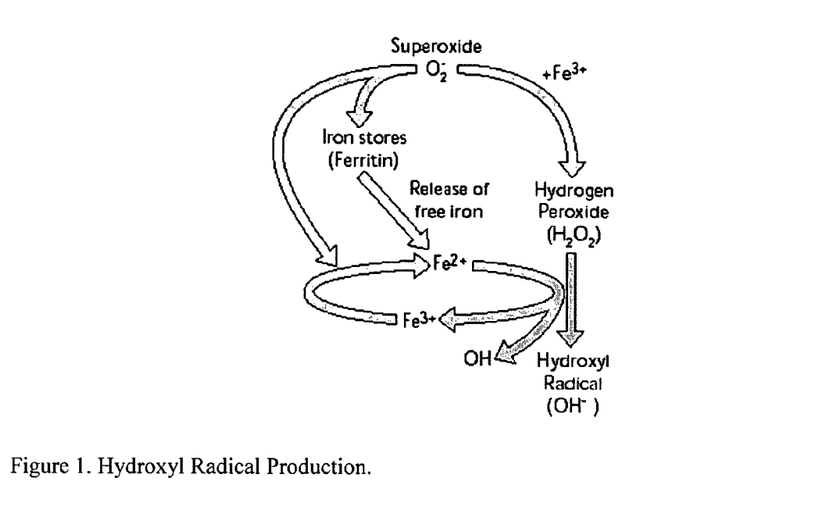
FIG. 1 illustrates the overall mechanism of hydroxyl radical production and regeneration.

This reaction is known as the Fenton reaction (Fenton, H.J.H., *J. Chem. Soc.*, 65, 899 (1894)). Hence, Reaction 4 generates ferric lixiviant for Reaction 3 thereby establishing a cyclic process. Reactions 3 and 4 are commonly referred to as the Haber-Weiss reaction (Haber, F. & Weiss J., *Proc. R. Soc. London Ser. A*, 147, 332 (1934)). The overall reaction mechanism is shown schematically in FIG. 1, below.

Accordingly, it can be concluded from the above that to maintain an ongoing iron-mediated Fenton reaction, an electron source must be available to regenerate the reduced metal, i.e., $Fe^{+3} \rightarrow Fe^{+2}$. In this invention, the membrane bound-enzymes NADH and NADPH are used for this purpose. Therefore, the presence of NAD(P)H ensures that ferric iron is reduced back to ferrous iron to maintain a more or less constant supply of chemical oxidants, thereby generating hydroxyl radicals via Reaction 4.

The underlying impetus or the "business end" of the present invention is the combination or the synergistic effect of the formation of chelated organic metal complexes R-M such as those found in U.S. Pat. Nos. 6,242,009 and 6,630,172 where such metals are anticancerous and/or microbicidal to pathogenic microorganisms and the concomitant generation of ROS or free radicals. Thus, the epitome of this invention is the synergism of these two factors. The ROS generating-system is preferably via Equation 4 discussed above.

One method of producing ROS can be through the breakdown of $H_2O_2$ to form hydroxyl radicals. There are a number of ways by which ROS may be formed from peroxide. The particular method of forming hydroxyl radicals from hydrogen peroxide is not critical to the present invention. The formation of hydroxyl radicals can be facilitated through any number of enzymatic or catalytic methods. More specifically, the formation hydroxyl radicals from hydrogen peroxide can be facilitated through the use of a reducing coenzyme which functions to reduce an oxidizing metal catalyst which thereafter reacts with a ROS generating species to produce ROS.

In preferred embodiments, my invention relies on contacting the microorganisms with a mixture comprising R-M such as those found in U.S. Pat. Nos. 6,242,009 and 6,630,172, and a system where continuous free radicals are generated whether in vivo or in vitro, depending on the circumstances. The free radical generating system is of paramount importance and comprises co-factors presented in sufficient amounts in milieu selected from nicotinamide adenine dinucleotide (NADH), nicotinamide adenine dinucleotide phosphate (NADPH) and/or flavin adenine dinucleotide (FADH) and flavin adenine dinucleotide phosphate (FADPH) to act as a source of electrons for the reduction of oxygen to give superoxide anion, and suitable oxidative disinfectant. The preferred oxidative disinfectant of the present invention is hydrogen peroxide. The amount of hydrogen peroxide added whether for in vivo or in vitro applications is designed to provide maximum anti-microbial activities. Damage to host cells and tissue can be circumvented by avoiding direct contact at periods of high exposures.

Other electron source such as thiols, ascorbate, paraquat, anthraquinone, quinone and semiquinone or redox-activating drugs such the antibiotic-antitumor bleomycin, amsacrine, mitomycin C, adriamycin, actinomycin D, daunomycine, neocarsinostatin, streptonigrin, elliptinium acetate, and the like or mixtures thereof can all be used as co-factors for the generation of ROS.

Other superoxide anion radicals ($.O^-_2$) generating schemes such as hypoxanthine or xanthine plus xanthine oxidase, (Beauchamp, C. & Fridovich, I., *J. Biol. Chem.*, 245, 4641 (1970)), and $Fe^{+2}$-(EDTA) systems (McCord, J. & Day, E., *FEBS Letters*, 86, 139 (1978)) can also be employed.

The ROS generating species may be added in any manner to the R-M and solvent, which permits the generating of the ROS. This may include simply adding a ROS disinfectant such as hydrogen peroxide. More preferably, a base is added to the R-M and solvent complex to alter the pH of the R-M and solvent complex. The base may be any base, and preferably is a non-toxic base, such as sodium hydroxide. The pH could be altered to any pH that allows for the production of ROS. For instance, the pH can be from about 7 to about 8, such as a pH from about 7.2 to about 7.6. Ideally, the pH would be buffered to the human physiological pH of about 7.4.

Once, or if the pH of the solvent has been adjusted, the solvent can be buffered by any suitable buffer. For example, a biological buffer that is preferably nontoxic to cells, such as ethylenediaminetetraacetic acid (EDTA), can be used. Once, or if the solvent has been buffered, a reducing cofactor and oxidizing metal catalyst may be added in any effective amount.

Furthermore, the method of preparation can further comprise the addition of metal catalysts for the enhancement of free radical generation. Preferably, ferric iron or salts thereof (e.g., ferric sulfate or soluble hexaaquoiron (III), $Fe(H_2O)_6^{+3}$) can be used for this purpose. Additionally, NADH and hydrogen peroxide can be added. These additions can result in an increased rate of ROS production. Furthermore, the present invention may also cause the stimulation of superoxide anion and hydroxyl radical (ROS) generation by living cells thereby enhancing the compositions' cytotoxic and microbicidal activities.

The formulations of the present invention can be used either directly, or can be diluted with aqueous solutions, like distilled and/or deionized water to provide the necessary cytotoxicity and biocidal activities, depending on the application.

Several DNA-intercalating agents can be added as well such as those associated with the ability to poison the enzymes topoisomerase I and topoisomerase II which are responsible for the interconversion of the topological states during DNA transcription and replication, and the regulation of DNA supercoiling. Examples of topoisomerase I poisons include protoberberines alkaloids and their synthetic analogs, coralyne, the benzo[c]phenanthridine alkaloids, nitidine (LaVoie, E. J., et al., The Second Monroe Wall Symposium on Biodiversity, Natural Product Discovery and Biotechnology, Simon Bolivar University, Caracas, Venezuela, January 7-9 (1998); Makhey et al., *Bioorg. & Med. Chem.*, 4, 781 (1996); Makhey et al., *Med. Chem. Res.*, 5, 1(1995); and Janin et al., *J. Med. Chem.*, 18, 708 (1975)), as well as the fungal metabolites, bulgarein (Fujii et al., *J. Biol. Chem.*, 268, 13160 (1993)), camptothecin and its derivatives topotecan and irinotecan, bi- and terbenzimidazoles (Bailly, C., *CMC*, 7, No. 1, 39 (2000); Kim et al., *J. Med. Chem.* 1996, 39, 992 (1996); Sun et al., *J. Med. Chem.* 1995, 38, 3638 (1995); and Chen et al., *Cancer Res.*, 53, 1332 (1993)), indolocarbazole derivatives (Bailly, C., *CMC*, 7, No. 1, 39 (2000); and Yamashita et al., *Biochemistry*, 31, 12069 (1992)), and saintopin (Yamashita et al., *Biochemistry*, 30, 5838 (1991)). Other topoisomerase I poisons are β-lapachone, diospyrin, topostatin, topostin, favonoids, Hoechst 33258 and the like and mixtures thereof. Examples of topoisomerase II poisons include teniposide or epipodophyllotoxin, VP-16 and VM-26, and podophyllotoxin-acridine conjugates-pACR6 and pACR8 (Rothenborg-Jensen et al., *Anti-Cancer Drug Design*, 16, 305 (2001)), and the like and mixtures thereof.

Certain embodiments of the present invention include angiogenesis inhibitory drugs such as angiostatin (O'Reilly, M., et al., *Cell*, 79, 315 (1994)) and endostatin (O'Reilly, M., et al., *Cell*, 88, 1 (1997)), or mixtures thereof.

In particular embodiments, the present formulation may include antimicrobial agents such as, but not limited to, acyclovir, chloramphenicol, chlortetracycline, itraconazole, mafenide, metronidazole, mupirocin, nitrofurazone, miconazole, magainins, cecropins, defensins, oxytetracycline, penicillin, and tetracycline; hormones such as, but not limited to, adrenocorticosteroids, cortisone, cortisol, betamethasone benzoate, betamethasone valerate, desonide, fluocinolone acetonide, halcinonide, and hydrocortisone; sedatives, hypnotics and tranquilizers such as, but not limited to, metandienone, benzocaine, dibucaine, lidocaine, pramoxine hydrochloride and tetracacine, pentobarbital sodium, phenobarbital, secobarbital sodium, carbromal, sodium phenobarbital, reserpine, and thiopropazate hydrochloride; topically active drugs (e.g., local anesthetics or anti-pruritics) such as, but not limited to, isotretinoin, benzoyl peroxide, salicylic acid, and tetracycline; analgesics such as, but not limited to, camphor, and menthol; vasodilating substances such as tolazoline; thrombosis-hampering substances such as heparin; certain biological substances which affect tissue formation and tissue stabilization such as EGF (epidermal growth factor), EGF-URO (EGFurogastron), and somatotropin asellacrine; sunscreens such as hydroquinone, monobenzone; and cleansing agents such as soaps and shampoos, and antiperspirants.

Also contemplated of the present invention is the inclusion of various antiviral agents. Examples of these agents include 9-(2-Hydroxyethoxymethyl)guanine, ZOVIRAX (GlaxoWellcome), idoxuridine, trifluorothymidine, bromovinyldeoxyuridine, ribavirin, amantadine, rimantadine, nevirapine (NVP), and the like.

Medical devices where the formulations can be used include, but are not limited to, medical implants such as urinary catheters, intravascular catheters, dialysis shunts, wound drain tubes, skin sutures, vascular grafts implantable meshes, intraocular devices, heart valves, and the like; wound care devices such as general wound dressings, biologic graft materials, tape closures and dressings, and surgical incise drapes and the like; drug delivery devices, and body cavity and personal protection devices such as skin patches, mucosal patches and medical sponges, and the like, and personal protection devices such as tampons, sponges, surgical and examination gloves, and toothbrushes, and the like; and birth control devices such as diaphragms and condoms, and the like.

The techniques and methods for incorporating the pharmaceutical formulations of the present invention to medical devices are well known to those skilled in the art.

The pharmaceutical composition of the present invention can have different forms such as, solutions, gels, and solids. The compositions can be bottled or packaged via a variety of types of dispensers to further facilitate its usefulness. For Example, for solutions, a bottle with a dropper is most convenient for eye drops, eardrops and nose drops. Alternatively, a pump spray makes it very convenient to apply the product externally and also provides a convenient and efficient method for oral use. Other forms of packaging can be readily apparent to those skilled in the art. With respect to the material of packing, such material should preferably be made of opaque glass containers, stainless steel containers, or in polypropylene or polyethylene plastic containers, and the like.

It will be apparent to those skilled in the art that the complexes described herein can be administered via controlled release metering devices. The methods and devices include biodegradable polymers, creams, lotions, liposomes, gels, capsules, pumps, syringes, infusion devices, and the like.

In one embodiment, the compositions further comprise metal catalytic activities for the enhancement of generating free radicals, and organic chelates, depending on application and severity of contamination. Preferably, ferric iron or its salts thereof can be used as the catalytic metal though other similar metals can be used as well. The addition of exogenous NADH and hydrogen peroxide results in stimulated superoxide anion and hydroxyl radical (ROS) generation by living cells thereby enhancing the compositions' cytotoxic and microbicidal activities. The present system can be represented symbolically as R-M-Fe(III)-NAD(P)H—$H_2O_2$, R and M were previously defined.

With respect to the organic part R, the metal ion(s) M complexes with for example potassium sodium tartrate (referred to thereafter as "PST-M") described in U.S. Pat. No. 6,630,172, incorporated in its entirety by reference herein. The amount of the PST used in the preparation of the solution can vary, depending on the metal and the acid being used. Preferably, not more than one fourth of the equimolar portion of the PST with respect to M is preferably used, depending on the valency of the M.

Other organic complexes can be used in addition to or in combination with the PST-M complex such as the R-M complexes described in U.S. Pat. No. 6,242,009 incorporated in its entirety by reference herein. When additional complexes are used, the R group may also include at least one amino acid or can be formed from at least one amino acid. The amino acids are preferably amphoteric, that is, they can react either as acids or as bases, depending on the circumstances. Preferably, examples of amino acids or compounds containing amino acids that can be used as the R group or to form the R group include, but are not limited to, alpha-amino acids. Specific examples include, but are not limited to, isoleucine, phenylalanine, leucine, lysine, methionine, threonine, tryptophan, valine, alanine, glycine, arginine, histidine, hydroxyproline, alpha-aminobutyric acid, asparagine, aspartic acid, cysteine, glutamic acid, glutamine, phenylalanine, proline, serine, tyrosine, and derivatives thereof such as ethylenediaminetetraacetic acid (EDTA), nitrilotriacetic acid (NTA), trans-diaminohexanetetraacetic acid (DCTA), bis(aminoethyl)glycolether-N,N,N',N'-tetracetic acid (EGTA), and the like, and mixtures thereof.

Optionally, the PST in the complex of the present invention can replace partially or entirely the amino acid group in the R-M complex described above. By using the PST, the resulting composition preferably potentiates the effect of controlling tumors and/or pathogenic microorganisms. By potentiating the antitumoral and/or the microbicidal compositions of the present invention, lower concentrations of heavy metals can then be used to achieve a certain efficacy. Accordingly, the use of the PST and the like preferably reduces any possible detrimental and deleterious effects of these metals on the recipient.

With respect to the other part of the complex that is M, M represents at least one monovalent or polyvalent metal ion or cation, which is anticanerous and/or antimicrobial to at least one microorganism. Preferably, the metal ion is anticancerous and/or microbicidal to a multitude of microorganisms. Examples of the metal ion include, but are not limited to, cations of silver including colloidal silver, copper, zinc, mercury, manganese, chromium, nickel, cadmium, arsenic, cobalt, aluminum, lead, iron, rhodium, iridium, selenium, platinum, gold, titanium, tin, barium, bismuth, vanadium, iron, strontium, antimony, and the like, and their mixture and their salts thereof.

Of course, the formulations of the present invention can be used either directly, or can be diluted with aqueous solutions, like distilled and/or deionized water to provide the necessary cytotoxicity and biocidal activities, depending on the application.

Under physiological conditions, ferric iron is slightly soluble and form precipitates with anions such as hydroxyl and phosphate ($Fe(OH)_3$ and $FePO_4.2H_2O$ with $K_{sp}$ equaling $1.6 \times 10^{-39}$ and $4 \times 10^{-27}$, respectively) with an estimated equilibrium concentration of $10^{-18}$ M (Spiro, T. G. & Saltman, R. In *Iron in Biochemistry and Medicine*, Vol. 1 (Jacobs, A. & Worwood, M., eds), pp 1-28, Academic Press, NY, 1974). Owing to the low solubility of iron under physiological pH, and to ensure the availability of iron thereby sustaining the pertinent reaction schemes, the composition of the present invention is preferably accomplished by forming it under low pH conditions (e.g., acidic conditions) and preferably at a pH of 2.0 or less. It is important to mention here that proportioning the complex to at-use concentrations should not affect the solubility of iron since complexation is irreversible in the present case.

In some embodiments, the compositions comprise one or more surfactants or detergents as wetting agents. It is contemplated that such surfactants are considered harmless and act as inert for example those found in the food and pharmaceutical industry such as sodium tripolyphosphate and the like, and can be anionic and/or non-anionic.

In certain other embodiments, the compositions can be mixed with other disinfectants, including, but not limited to, isopropanol, chlorhexidine gluconate, chlorhexidine digluconate, chlorhexidine dihydrochloride, and/or chlorhexidine diacetate though it is not necessary. In addition, natural and artificial colors and flavors as well as other additives can be added as well.

In still another preferred embodiments of the present invention, the compositions are nontoxic, nonirritant and noncorrosive while possessing cytotoxicity, potency and killing efficacy against a broad spectrum of pathogens.

In the preferred process of making the organic complex of the present invention, a metal complex of the formula R-M is prepared in accordance with U.S. Pat. No. 6,242,009 and/or U.S. Pat. No. 6,630,172. Then, the ROS generating-system is prepared at pH of 2.0 or less, by mixing a reducing agent (e.g., NADH), a ferric iron salt (e.g., ferric sulfate) or soluble hexaaquoiron (III), $Fe(H_2O)_6^{+3}$, and an acidic agent (e.g., phosphoric acid), at room temperature (e.g., 25° C.) and preferably in the presence of an aqueous solution like distilled-deionized water. Then, the organic containing compound such as PST alone or with amino acid forms the metal complex preferably while homogenizing the mixture. This preparation preferably occurs under low pH conditions, such as at a pH of 2.0 or less. The resulting solution can then be further diluted with aqueous solution and preferably distilled-deionized water and further disinfectants or other additives can be added to form the microbicidal compositions of the present invention. The aqueous solution may be condensed and dried using conventional methods available to those skilled in the art to produce gels as well as solids, such as tablets or powders. Thus, this composition, for example, in the form of a tablet, pill, capsule, mass of particles and the like, may be combined with, e.g., placed into a liquid medium, such as described elsewhere herein. Solid forms include tablets, capsules, suppositories, and the like or mixtures thereof. For oral administration, basic sugars, starch, enteric coating and the like can be added to the composition. The composition of the present invention may be conveniently provided in a liquid carrier. Any liquid carrier may be employed provided that such carrier should behave as an inert, that is, should not chemically interfere with the chemical constituents of the composition. Other delivery routes will be readily apparent to those skilled in the art. In addition, the solid form of the present compositions may be activated upon solubilization in a liquid.

In the case of in vivo application, certain embodiments of the present compositions are nontoxic to humans and animals, and therefore can be safely ingested or administered to human and animal to subjects via nasal, buccal, vaginal, rectal, and topical, and can be contacted via subcutaneous, intradermal, intramascular injections or any other effective route to the site of infection, preferably the route of administration be designed to obtain direct contact with the condition being treated. The compositions further comprise pharmaceutically acceptable stabilizers, adjuvants, diluents, bioactive chemicals such as antivirals, antibiotics, vitamins, minerals, and mixtures thereof, and other components that are well known to those skilled in the art. Carriers for topical applications may take the form of liquids, gels, foams, lotions and the like and can comprise organic solvents such as ionic and/or nonionic surfactants, perfumes, dyes and the like, and other ingredients commonly used in the pharmaceutical industry which are approved for such uses. Again, such carriers should act as inert. Other routes of delivery of the present compositions to the site of infection include impregnation into absorptive materials, e.g., bandages, gauze, or coating on solid phase materials such as zippers, staples, and the like.

In another embodiment, the present invention can be stored in a non-reactive state by not allowing all components of the system to combine under conditions where the synergistic and the catalytic effect can occur through methods available to those skilled in the art. Activation of the disclosed compositions can then be done by the user at the site of application.

By the term "chemotherapeutic" as used within the present context is meant the inhibition of the growth of cancer cells which are sensitive to the compositions disclosed herein, viz., therapy involving the administration of an effective amount of the subject invention. Preferably such treatment also leads to regression of cancerous cells. Most preferably, such treatment leads to the complete regression of cancerous cells. By the term "cytotoxic" as used here is meant the degree to which something is toxic to living cells.

According to the present invention, controlling the growth of at least one microorganism includes both the reduction and/or prevention of such growth. It is to be further understood that by "controlling," the growth of at least one microorganism is inhibited. In other words, there is no growth or substantially no growth of at least one microorganism. "Controlling" the growth of at least one microorganism includes maintaining a microorganism population at a desired level (including undetectable levels such as zero population), reducing a microorganism population to a desired level, and/or inhibiting or slowing the growth of at least one microorganism. Thus, materials and mediums susceptible to attack by at least one microorganism are preserved and/or protected from this attack and the resultant deleterious effects. The present invention also provides a method for controlling the growth of at least one microorganism in or on a material or medium susceptible to attack by the microorganism, which comprises the step of adding to the material or medium a composition of the present invention in an amount effective to control the growth of the microorganism.

The mode as well as the rates of application of the composition of this invention could vary depending upon the intended use. The composition could be applied by spraying or brushing onto the material or product. The material or product in question could also be treated by dipping in a suitable formulation of the composition. In a liquid or liquid-like medium, the composition could be added into the medium by pouring or by metering with a suitable device so that a solution or dispersion of the composition can be produced. Thus, the substrates or materials susceptible to attack by these types of microorganisms are preserved from this attack and the resulting spoilage or other detrimental effects caused by the microorganisms. Further, it is to be understood that "controlling" the growth of at least one microorganism also includes biostatically reducing and/or maintaining a low level of microorganisms such that the attack by microorganisms and any resulting spoilage or other detrimental effects are mitigated, i.e., the microorganism growth rate or microorganism attack rate is slowed down or eliminated. Hence, the concentrations of the present invention depend on many factors, including site of treatment, the desired response and duration of the composition's action, and other factors that will be apparent to those skilled in the art.

Microorganisms, as used herein, include, but are not limited to bacteria, both gram-positive and -negative, fungi, algae, viruses, amoebae, spores, and the like, and include both yeast and molds.

The present invention is further illustrated by the following representative and non-limiting examples. These experiments constitute some of the embodiments of the invention disclosed herein. The main impetus behind these examples is solely for the purpose of illustration and is in no way of limitation.

EXAMPLES

Materials and Methods
Chemicals:

The $NADHNa_2$, ferric sulfate, glutamic acid (GA), silver nitrate, 85% phosphoric acid, and 3% hydrogen peroxide used to prepare the compositions of the present invention were purchased from Sigma-Aldrich, and all were pharmaceutical grade degree of purity. Their molecular weights are given in Table 1.

TABLE 1

Molecular Weights (MW) of Chemicals Used.

| Chemicals | MW (g/g-mol) |
|---|---|
| 3% Hydrogen Peroxide | 18.26 |
| Glutamic Acid | 147.13 |
| Silver Nitrate | 169.9 |
| $NADH(Na)_2$ | 709.4 |
| Ferric Sulfate | 399.9 |

Preparation of the Composition of the Present Invention:

The R-M complex was prepared in accordance with published U.S. Pat. No. 6,242,009. At room temperature, and under minimum light, 0.51 ml of 85% $H_3PO_4$ was added to 4.09 ml of doubled distilled-de-ionized water. By using a micropipette, three equal aliquant each of 1.0 ml of this prepared solution were placed into 3 sterile tubes, Tubes 1, 2 and 3. For the first two tubes (Tubes 1 and 2), 174 mg of $AgNO_3$ was added, followed by 150 mg of GA, representing U.S. Pat. No. 6,242,009-Sample #1 (Row 1 in Table 2). Instantly, yellowish precipitates are formed. In Tube 3, 44 mg of $Fe_2(SO_4)_3$ was added, followed by 32.4 mg of GA. Light-yellow precipitates are formed. Then, Tubes 2 and 3 were mixed thoroughly, thereafter referred to as Tube 4, Sample #2. Following that, 184 µl of Tube 1 and 368 µl (to account for mixing 1.0 ml of Tube 2 and 1.0 ml of Tube 3) of Tube 4 were transferred and placed in plastic tubes and mixed with 40 ml of doubled distilled-de-ionized water where it was stirred continuously until homogenization was achieved. The colors of both samples did not change. This resulted in solutions with a pH of about 2.0. The pH was adjusted to its physiological value (pH=7.4) with the addition of phosphate buffer saline and EDTA. Then, 10 ml portions of Samples #1 and #2 were placed into sterile tubes where the designated amounts of $NADHNa_2$ and $H_2O_2$ identified in Table 2 were added, and mixed thoroughly. This was done at pH=7.4 since low pH leads to the decomposition of $NADHNa_2$.

TABLE 2

Weights (mg) and Volumes (ml) of Chemicals Used to Test Efficacy.

| Sample # | $NADHNa_2$* | $Fe_2(SO_4)_3$ | GA | 3% $H_2O_2$ | Reference |
|---|---|---|---|---|---|
| 1 | 0.0 | 0.0 | 150.0 | 0.6 | U.S. Pat. No. 6,242,009 |
| 2 | 14.1 | 44.0 | 32.4 | 0.6 | Present Invention |
| 3 | 0.0 | 0.0 | 0.0 | 0.6 | 50 mM |

*The addition of $NADHNa_2$ was done at pH of 7.4 to avoid its acid decomposition (Kaplan, N. O., *Enzymes*, 3, 105 (1960)).

The samples were then submitted for biological assays for the evaluation of MIC. It is important to note here that the same batch was used for all the experiments so as to minimize experimental errors. It is further noted that all dilution factors were taken into consideration throughout the preparation of the antimicrobial composition as depicted in Table 2.

For comparative purposes, the MIC values for the antibiotics Gentamicin (GEN)-effective against gram-positive and negative bacteria, Oxacillin (OXA)-effective against gram-positive bacteria, and equal amounts of Penicillin (PEN)-effective against gram-positive and negative bacteria and streptomycine (STR)-effective against gram-positive and negative bacteria, and mycobacteria, were also evaluated. In addition, the MIC value for 50 mM of hydrogen peroxide were also evaluated by mixing 0.6 ml of 3% $H_2O_2$ with 10 ml of distilled-de-ionized water, Sample #3 (Table 2).

I. As an Antibiotic:
Microorganisms:

The bacteria used to test the efficacy on the present compositions were the gram-positive *Staphylococcus aureus* (*S. aureus*) ATCC 43300 and an extremely tenacious strain of gram-negative *Escherichia coli* (*E. coli*) that did not respond to many conventional antibiotics, which was procured from a patient who was suffering from severe gastroenteritis.

Biological Assays:

Unless otherwise indicated, cells were challenged with the composition of the present invention at a density of $1 \times 10^7$ CFU/ml at 37° C. Cell suspension concentration was calculated by measuring the optical density ($A_{610}$) between 0.6 and 0.9.

3.125, 1.562, 0.781, 0.391, and 0.195%. These tubes were then incubated at 37±2° C. for approximately 24 hours without agitation. The tubes were then observed for presence and level of visible growth. The test culture was also inoculated into Muller Hinton media (without disinfectant) to show that it was capable of rapid growth and that the growth medium was good. The growth medium was incubated (in test-tubes and in the original bottles) to show that it and the glassware were sterile. All controls turned out as expected, validating the observations of the actual experiment.

Prior to discussing the results, several experimental observations merit special mention with respect to mixing. For the preparation of the present invention (Sample #2), it is prudent to formulate the invention in two separate steps, namely, the preparation of the silver solution (Tube 2 above), and the iron solution (Tube 3 above) must be done separately, then the two are mixed together. If the mixture is prepared all at once, lower MIC values by almost $2^3$ are obtained in comparison with that of the present invention's formulation sequence.

The efficacy or MIC results obtained are given in Table 3. These data unequivocally demonstrate the superiority of the present invention in comparison with the antibiotics tested here with respect to its antimicrobial spectrum and effectiveness.

TABLE 3

MIC Results.

| | | E. coli | | | | | S. aureus (ATCC 43300) | | | |
|---|---|---|---|---|---|---|---|---|---|---|
| % of initial | GEN | PEN:STR 55%:45% | OXA | 50 mM $H_2O_2$ | Present Invention | 50 mM $H_2O_2$ | U.S. Pat. No. 6,242,009 | Present Invention | OXA | GEN |
| 100 | + | + | + | NG | NG | + | NG | NG | NG | NG |
| 50 | + | + | + | NG | NG | + | NG | NG | NG | NG |
| 25 | + | + | + | NG | NG | + | NG | NG | NG | NG |
| 12.5 | + | + | + | + | NG | + | NG | NG | NG | NG |
| 6.25 | + | + | + | + | NG | + | + | NG | NG | NG |
| 3.125 | + | + | + | + | NG | + | + | NG | NG | NG |
| 1.562 | + | + | + | + | NG | + | + | NG | NG | NG |
| 0.781 | + | + | + | + | NG | + | + | NG | NG | NG |
| 0.391 | + | + | + | + | NG | + | + | + | + | NG |
| 0.195 | + | + | + | + | + | + | + | + | + | NG |

Notes:
"+" denotes visually detectable growth in MIC tube.
"NG" denotes "no growth" in MIC tube: bold and underlined "NG" denotes the MIC values.

To study efficacy, the challenge was done by determining minimum inhibitory concentration or MIC by employing serial dilutions. The minimum inhibitory concentration or MIC is defined as the minimum concentration of antibiotic that will inhibit the growth of the isolated microorganism. In its normal mode of operation, a bacterial inoculum is inoculated into tubes containing culture media and varying concentrations of the antibiotic to be tested. The tubes are incubated to allow bacterial growth. The MIC is read as the lowest concentration of biocide that inhibited bacterial growth. The interpretation of this MIC depends on the organism/biocide pair being tested, and is made following standard guidelines. MIC testing of the present compositions was conducted via a macrodilution procedure using NCCLS (National Committee for Clinical Laboratory Standards) methods for antibiotic susceptibility testing. The biological experiments were conducted by serial dilution with Muller Hinton media of ten tubes where the bacterial concentration was 10 million cells/ml in each. In addition to the "as is" samples (i.e. 100%), ten 1:1 serial dilutions of each sample were tested to determine the MIC for each sample-inoculum combination. The equivalent percentages of the dilutions are: 100, 50, 25, 12.5, 6.25, The initial concentrations used for GEN, PEN:STR and OXA are 400, 60:50, and 400 ppm, respectively, while the initial concentrations of silver and ferric iron are 500 and 52 ppm, respectively (the total is 552 ppm). Based on the MIC values given in Table 3 above, it is possible to calculate the concentrations of each antibiotic tested here. A comparison of MIC values is given in Table 4.

TABLE 4

A Comparison Between the MIC Values in ppm for the Different Antibiotics Tested with the Present Invention.

| Bacteria | GEN | PEN:STR | OXA | Present Invention Ag:Fe |
|---|---|---|---|---|
| E. Coli | NE | NE | NE | 0.977:0.102 |
| S. aureus | 0.391 | — | 1.56 | 1.953:0.203 |

"NE" denotes not effective.

By comparing the values of MIC for *S. aureus*, it can be concluded that the concentration of the present invention with respect to iron and silver are comparable to those of the other antibiotics used. Notice here that the other antibiotics used did not have any effect on the E coli strain while the present invention gave excellent antibiotic activities.

II. As a Chemotherapeutic Agent:

Example 1

The cytotoxic effect of the present invention on Vero (Simian Kidney Immortalized Cell Line), and MCF-7 (mammary gland; breast; epithelial; from metastatic site: pleural effusion adenocarcinoma) was evaluated. Cells are plated in a 96 well flat bottom tissue culture plates at 10,000 cells/well. Dilutions and controls are added to wells as follows:

| 1. | $10^4$ Cells 100 μl | +Media 100 μl |
|---|---|---|
| 2. | = | +1:4 Present invention |
| 3. | = | +1:8 |
| 4. | = | +1:16 |
| 5. | = | +1:32 |
| 6. | = | +1:64 |
| 7. | = | +1:128 |
| 8. | = | +1:256 |
| 9. | = | +1:512 |
| 10. | = | +1:1024 |
| 11. | = | +1:2048 |
| 12. | = | +Cisplatin 8 μM |
| 13. | = | +Cisplatin 4 μM |

Vero Cells were grown and tested in complete Dulbeco's Modified Eagles Medium (DMEM) supplemented with 15% Fetal Bovine Serum (FBS), Gentamicine 40 μg/ml, Hepes buffer at pH=7.2, L-Glutamine 2 mM and Sodium pyruvate. MCF-7 were grown and tested in complete RPMI-1640 medium supplemented with 10% FBS Gentamicine 40 μg/ml, Hepes buffer at pH=7.2, L-Glutamine 2 mM and Sodium pyruvate. Plates were incubated in CO2 in a humidified incubator at 37° C. for 72 hrs, and then each well was harvested and counted by Trypan Blue dye exclusion method. Numbers of viable cells were counted on a hemacytometer and adjusted for concentration of cells/ml. For comparative purposes, experiments with Cisplatin (C12H6N2Pt, MW=300), a well-known chemotherapeutic drug, at 8 and 4 μM were also conducted.

Figure 2:
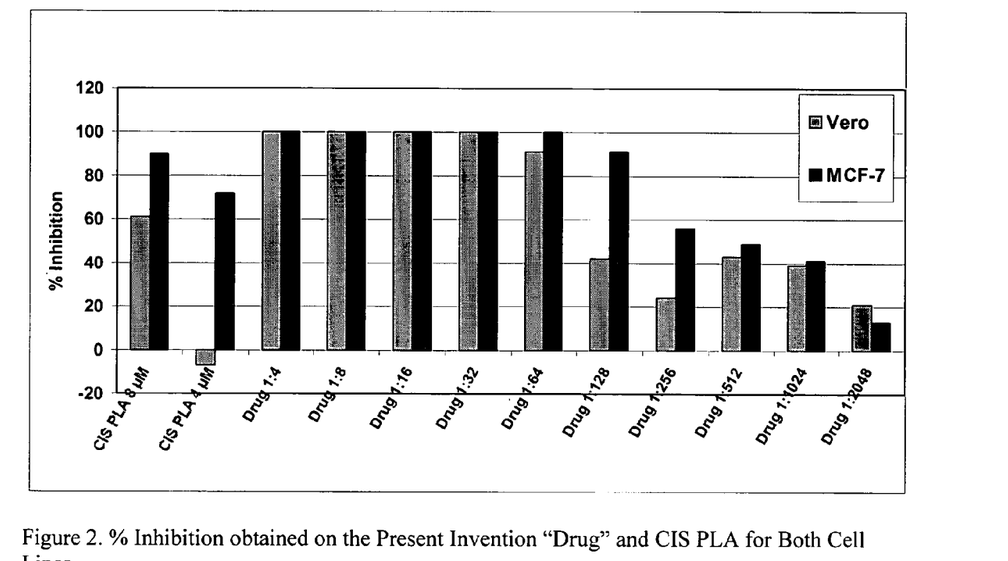
FIG. 2 is a chart detailing the results of effectiveness comparisons.

The results obtained are shown in FIG. 2 and Table 5. The terms "Drug" and CIS PLA refer to the present invention and Cisplatin, respectively.

TABLE 5

% Inhibition Obtained on the Present Invention "Drug" and Cisplatin for Both Cell Lines.

| | ppm | | % Inhibition | |
|---|---|---|---|---|
| Dilution | Ag | Fe | Vero | MCF-7 |
| Drug 1:4 | 125 | 13 | 99 | 100 |
| Drug 1:8 | 62.5 | 6.5 | 98 | 100 |
| Drug 1:16 | 31.25 | 3.25 | 97 | 97 |
| Drug 1:32 | 15.625 | 1.625 | 100 | 95 |
| Drug 1:64 | 7.812 | 0.812 | 91 | 46 |
| Drug 1:128 | 3.906 | 0.406 | 42 | −8 |
| Drug 1:256 | 1.953 | 0.203 | 24 | 13 |
| Drug 1:512 | 0.977 | 0.102 | 43 | 49 |
| Drug 1:1024 | 0.488 | 0.0508 | 39 | 41 |
| Drug 1:2048 | 0.244 | 0.0254 | 21 | 13 |
| CIS PLA 8 μM | | | 61 | 90 |
| CIS PLA 4 μM | | | −7 | 72 |

Careful examination of FIG. 2 reveals that at lower dilution rates (higher concentrations), the present invention "Drug" exhibits similar cytotoxicity on Vero and MCF-7 cell lines, up to a dilution rate of 1:32, corresponding to 17.25 ppm. In the dilution range of 1:64 to 1:1024 (8.625-0.5388 ppm), the cytotoxic effect becomes less significant for Vero in comparison with that for MCF-7.

A quantitative comparison at similar concentrations between the present invention and platinum in Cisplatin at 8 and 4 μM with respect to the amounts of silver and iron at 1:512 and 1:1024 dilutions, corresponding to 9 μM (500/(108×512))×$10^3$ silver and 1.82 μM (52/(55.8×512))×$10^3$ iron, and 4.5 μM (9/2) of silver and 0.91 μM (1.82/2) of iron is given in Table 6. The molecular weights of silver and iron are 108 and 55.8, respectively.

TABLE 6

% Inhibition Between the Present Invention at 1:512 and 1:1024 Dilutions and Platinum in Cisplatin with respect to the Amounts of Metal in μM on Chemotherapeutic Activities.

| | Pt in Cisplatin | | Present Invention | |
|---|---|---|---|---|
| | | | Ag (9 μM):Fe | Ag (4.5 μM):Fe |
| | 8 μM | 4 μM | (1.82 μM) | (0.91 μM) |
| Vero | 61 | −7 | 43 | 39 |
| MCF-7 | 90 | 72 | 49 | 41 |

It can be deduced from Table 6 that the present invention gives comparable results to that of Cisplatin. Notice here that at 4 μM of Cisplatin, there was no effect on the Vero cell lines while the present invention resulted in 39% inhibition.

Example 2

The cytotoxic effect of the present invention was also evaluated on MCF-7, T-47D (mammary gland; breast; duct; from metastatic site: pleural effusion ductal carcinoma), BHL-89 (Human B-type EBNA negative lymphoma) and Jurkat (T-lymphocyte; acute T-cell leukemia), and compared with cyclophosphamide, which is another chemotherapeutic agent. The methodology was the same as the one employed for Example 1 above. The results are given in FIG. 3, below.

Figure 3:
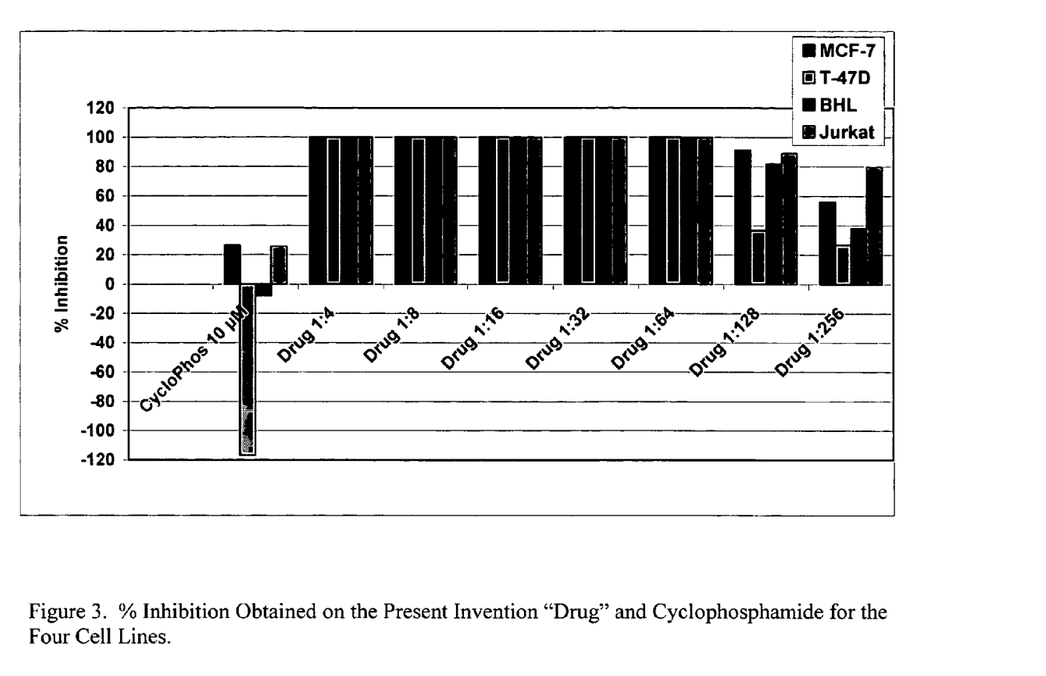
FIG. 3 is a chart detailing the results of effectiveness comparisons.

By examining FIG. 3, it can be concluded that the present invention "Drug" gives excellent cytotoxic activities, especially against BHL-89, and T-47D in comparison with cyclophpsphamide, Cyclophos. This effect is pronounced even at the lowest dilutions, corresponding to a dilution of 1:256, which is equivalent to 18 and 3.64 μM of silver and iron, respectively. Actually, cyclophosphamide does not have any effects on both of these cell lines at the specified dilution and minimum effects on both MCF-7 and Jurkat.

With regard to the present invention, the uniqueness of silver in comparison with other antimicrobial-chemotherapeutic metals is the fact that silver in low concentrations has no toxicity and carcinogenic activities and exhibits an excellent clinical tolerance (Furst, A. & Schlauder, M. C., *Journal Environmental Pathology and Toxicology*, 1, 51 (1978)). The body is protected from silver toxicity by the blood-brain barrier. Also, ubiquitous metalothioneins proteins, which is present in all living organisms, have the property of binding silver in metal thiolate cluster structures to transport, store, and detoxify essential and nonessential trace metals that may enter the body (Stillman, M. J., et al., *Metal-Based Drugs*, 1, 375 (1994)). Knowing the fact that silver has a much safer tolerance record than most heavy metals, especially those belonging to the family of oxaliplatin, this makes the current invention very attractive to implement. Therefore, it is possible, with the aid of the present invention to design therapeutic agents that employ silver and iron, rather than the currently used heavy metals, and conventional therapy. The many adverse side effects associated with the current systemic therapeutic methods used for the treatment of cancer such as radiation, immunotherapy, chemotherapy, and antiangiogenic drugs can therefore be alleviated, which makes the present invention an excellent candidate for alternative therapy.

ADDITIONAL REFERENCES

Aitken, R., U.S. Pat. No. 6,433,002 (2002).
Britigan, B., et al., *Biochimica et Biophysica Acta,* 1290, 231 (1996).
Gutman, M., & Eisenbach, M., *Biochemistry,* 12, 2314 (1973).
Imlay, J., et al., *Science,* 240, 640 (1988).
Imlay, J. & Linn, S., *J. of Bacteriology,* 166, 519 (1986).
Kessler, J., et al., U.S. Pat. No. 4,588,586 (1986).
Koppenol, W., *Free Radical Biology & Medicine,* 25, 385 (1998).
Land, E., & Swallow, J., *Biochimica et Biophysica Acta,* 234, 34 (1971).
Lindahl, T., *Nature,* 298, 424 (1982).
Luo, Y., et al., *Proc. Natl. Acad. Sci.,* 91, 12438 (1994).
Park, J., et al., U.S. Pat. No. 5,330,752 (1994).
Robinson, M., et al., *J. Surg. Res.,* 69, 325 (1997).
Spencer, J., et al., *FEBS Letters,* 374, 233 (1995).

All publications, patents, and patent applications mentioned herein form a part of the patent application and are incorporated in their entirety by reference herein.

The preceding discussion, examples, procedures, and specific salient features disclosed herein are solely intended for setting-up the general and certain preferred embodiments of the present invention. Thus, various modifications and suggestions in lieu thereof can be implemented by those skilled in the art. These should be an essential part of this application and can be made consistent with the letter and spirit of the foregoing disclosure, and within the true scope, merits and purview of this invention, which is presented by the following claims:

What is claimed is:

1. An anti-microbial composition consisting essentially of:
a) an anti-microbial amount of a chelated organic metal complex obtained by combining at least one metal salt and at least an equimolar amount of glutamic acid;
b) at least one reducing coenzyme and an equimolar amount of an oxidizing metal catalyst; and
c) an anti-microbial amount of hydrogen peroxide, wherein said metal salt has at least one metal which is microbicidal to at least one microorganism, and wherein the amounts of the reducing coenzyme and oxidizing metal catalyst are effective to oxidize the hydrogen peroxide.

2. The anti-microbial composition of claim 1, wherein said metal salt and said glutamic acid are first combined in a solvent containing an acid, and then a base is added to said solvent in an amount sufficient to bring the pH of said solvent to a range from about 6.8 to about 8, then said reducing coenzyme, said oxidizing metal catalyst and said hydrogen peroxide to produce free radicals are added to the solvent containing said metal salt and said glutamic acid.

3. The anti-microbial composition of claim 1, wherein said metal salt and said glutamic acid are first combined in a solvent containing an acid, a base is then added to said solvent in an amount sufficient to bring the pH of said solvent to a range from about 6.8 to about 8, then said reducing coenzyme and said oxidizing metal catalyst are added to said solvent, and finally said hydrogen peroxide to produce free radicals is added to said solvent within one hour of use.

4. The anti-microbial composition of claim 2, wherein said pH ranges from about 7.2 to about 7.6.

5. An anti-microbial composition consisting essentially of:
a) an anti-microbial amount of a chelated organic metal complex obtained by combining at least one metal salt and at least an equimolar amount of glutamic acid;
b) at least one reducing coenzyme and an equimolar amount of oxidizing metal catalyst; and
c) an anti-microbial amount of hydrogen peroxide, wherein said metal salt has at least one metal which is microbicidal to at least one microorganism, wherein said metal salt is a silver salt, wherein said coenzyme is NADH, NADPH, FADH or FADPH, wherein said oxidizing metal catalyst is ionic iron, wherein said pH ranges from about 7.2 to about 7.6, wherein said solvent is deionized water buffered with EDTA, and wherein the amounts of the reducing coenzyme and oxidizing metal catalyst are effective to oxidize the hydrogen peroxide.

6. The anti-microbial composition of claim 1, wherein said coenzyme is NADH, NADPH, FADH, FADPH, or combinations thereof.

7. The anti-microbial composition of claim 1, wherein said metal salt is a salt containing silver, copper, zinc, mercury, chromium, manganese, nickel, cadmium, arsenic, cobalt, aluminum, lead, selenium, platinum, gold, titanium, tin or a combination thereof.

8. The anti-microbial composition of claim 1, wherein said oxidizing metal catalyst is Cu, Fe, K, Mg, Mn, Mo, Ni, Se, Zn, or a combination thereof.

9. The anti-microbial composition of claim 1, further comprising at least one DNA intercalating agent.

10. The anti-microbial composition of claim 1, further comprising at least one angio-inhibitory agent.

11. The anti-microbial composition of claim 1, further comprising at least one anti-microbial agent.

12. The anti-microbial composition of claim 1, further comprising at least one chemotherapeutic agent.

13. The anti-microbial composition of claim 1, further comprising at least one anti-viral agent.

14. The anti-microbial composition of claim 1, further comprising at least one wetting agent or surfactant.

15. The anti-microbial composition of claim 1, further comprising at least one disinfectant.

16. The anti-microbial composition of claim 15, wherein said disinfectant is chlorhexidine gluconate, chlorhexidine digluconate, chlorhexidine dihydrochloride, chlorhexidine diacetate, isopropyl alcohol, hydrogen peroxide, potassium sodium tartrate (PST), or a mixture thereof.

17. A method of making the anti-microbial composition of claim 1 comprising, a) combining one metal salt and at least an equimolar amount of glutamic acid with an acid in a solvent, b) adding a base to said solvent in an amount sufficient to adjust the pH of said solvent to a range from about 6.8 to about 8, c) adding a buffer to said solvent, d) adding at least one reducing coenzyme, an equimolar amount of oxidizing metal catalyst, and hydrogen peroxide.

18. The method of claim 17, wherein metal salt is a silver salt, said solvent is de-ionized water, said buffer is EDTA or potassium sodium tartrate (PST), said reducing coenzyme is NADH or NADPH, and said oxidizing metal catalyst is an iron salt.

19. The method of claim 17, wherein said solvent is deionized water and said acid is present in an amount sufficient to initially lower the pH of said solvent to about 2.5 or below.

20. The method of claim 17, wherein the amount of said base is sufficient to adjust the pH of said solvent to a range from about 7.2 to about 7.6.

21. The method of claim 17, wherein the amount of said base is sufficient to adjust the pH of said solvent to about 7.4.

22. The method of claim 17, wherein said method is conducted at room temperature.

23. The method of claim 17, wherein said acid has a pH of 2.5 or lower.

* * * * *